US012660733B2

(12) United States Patent
Koch

(10) Patent No.: US 12,660,733 B2
(45) Date of Patent: Jun. 23, 2026

(54) HIGH AND LOW FREQUENCY SOIL AND PLANT ANALYSIS SYSTEMS WITH INTEGRATED MEASUREMENTS

(71) Applicant: Precision Planting LLC, Tremont, IL (US)

(72) Inventor: Dale M. Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 348 days.

(21) Appl. No.: 17/907,466

(22) PCT Filed: Feb. 2, 2021

(86) PCT No.: PCT/IB2021/050819
§ 371 (c)(1),
(2) Date: Sep. 27, 2022

(87) PCT Pub. No.: WO2021/214557
PCT Pub. Date: Oct. 28, 2021

(65) Prior Publication Data
US 2023/0119569 A1     Apr. 20, 2023

Related U.S. Application Data

(60) Provisional application No. 63/014,351, filed on Apr. 23, 2020.

(51) Int. Cl.
*A01B 79/00* (2006.01)
*G01N 23/223* (2006.01)
(Continued)

(52) U.S. Cl.
CPC ....... *A01B 79/005* (2013.01); *G01N 33/0098* (2013.01); *G01N 33/24* (2013.01);
(Continued)

(58) Field of Classification Search
CPC .. A01B 79/005; G01N 33/0098; G01N 33/24; G01N 23/223; G01N 31/227; G01N 33/245
See application file for complete search history.

(56) References Cited

U.S. PATENT DOCUMENTS 5,673,637 A     10/1997  Colburn, Jr. et al.
2007/0042803 A1 *  2/2007  Anderson ............ G05D 1/0225
455/556.1
(Continued)

OTHER PUBLICATIONS

Castrignano et al., "A Combined Approach of Sensor Data Fusion and Multivariate Geostatistics for Delineation of Homogeneous Zones in an Agricultural Field" Sensors 2017, 17, 2794 (Year: 2017).*
(Continued)

*Primary Examiner* — John C Kuan

(57) ABSTRACT

A soil or plant analysis apparatus to perform low and high frequency measurements is described herein. In one embodiment, the soil analysis apparatus comprises a first subsystem to perform low frequency soil measurements and a second sub-system to perform high frequency soil measurements. The high frequency measurements of the second sub-system are at least 1.25 times the low frequency measurements of the first sub-system.

15 Claims, 8 Drawing Sheets

(51) Int. Cl.
    *G01N 33/00*         (2006.01)
    *G01N 33/24*         (2006.01)
    *G01N 31/22*         (2006.01)

(52) U.S. Cl.
    CPC ......... *G01N 23/223* (2013.01); *G01N 31/227*
                (2013.01); *G01N 33/245* (2024.05)

(56)                References Cited

U.S. PATENT DOCUMENTS

| | | | |
|---|---|---|---|
| 2014/0379228 A1* | 12/2014 | Batcheller | A01C 7/201 |
| | | | 701/50 |
| 2017/0372642 A1 | 12/2017 | Hofecker | |
| 2018/0168094 A1* | 6/2018 | Koch | A01C 5/064 |
| 2019/0101505 A1* | 4/2019 | Liu | G01N 1/08 |
| 2019/0271656 A1 | 9/2019 | Pruessner | |
| 2020/0128721 A1* | 4/2020 | Lewis | G01N 33/24 |
| 2021/0190754 A1 | 6/2021 | Stoller et al. | |

OTHER PUBLICATIONS

UK Intellectual Property Office, Search report for related UK Application No. GB2006614.8, dated Nov. 5, 2020.
European Patent Office, International Search Report related to International Patent Application No. PCT/IB2021/050819, mail date May 3, 2021.

* cited by examiner

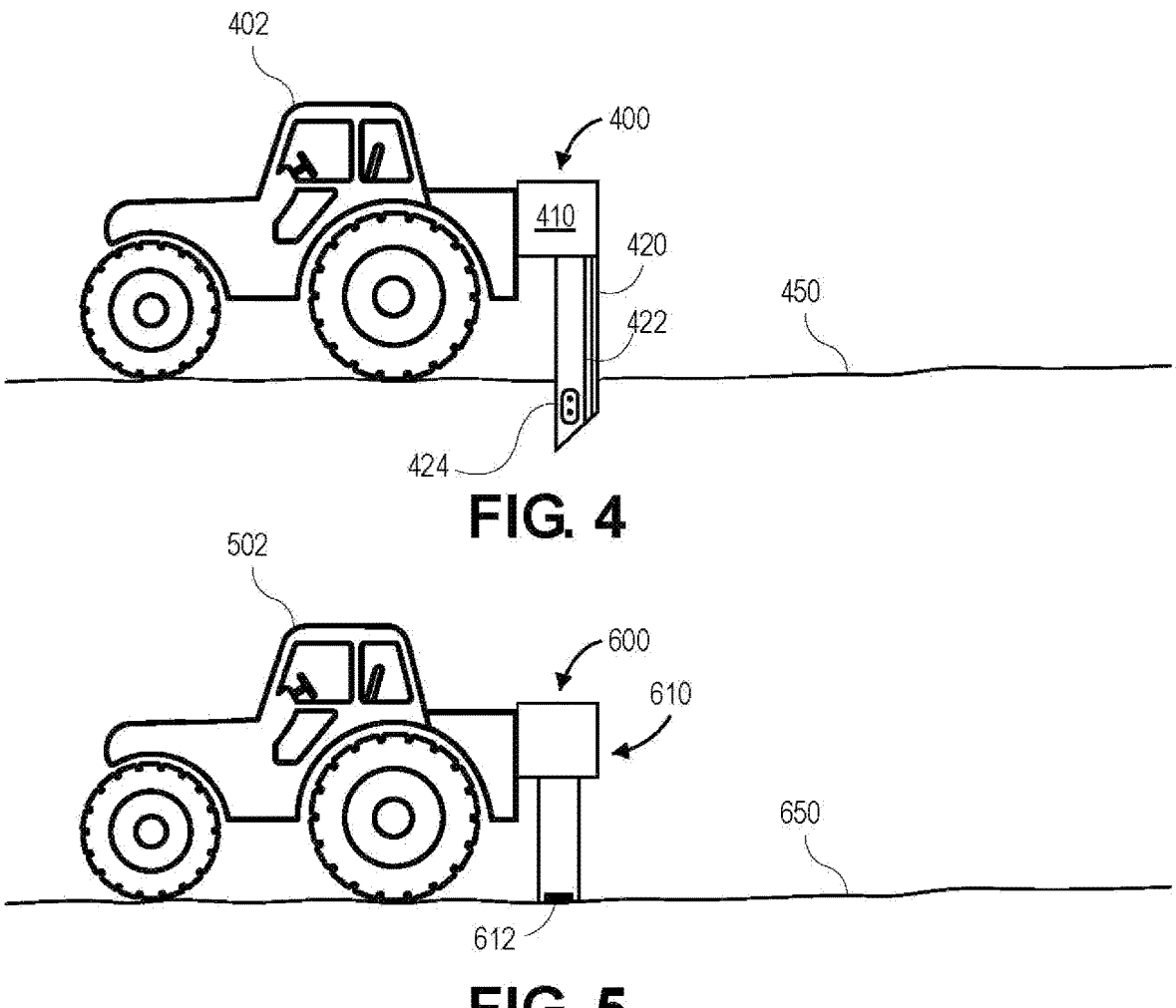
FIG. 4
FIG. 5
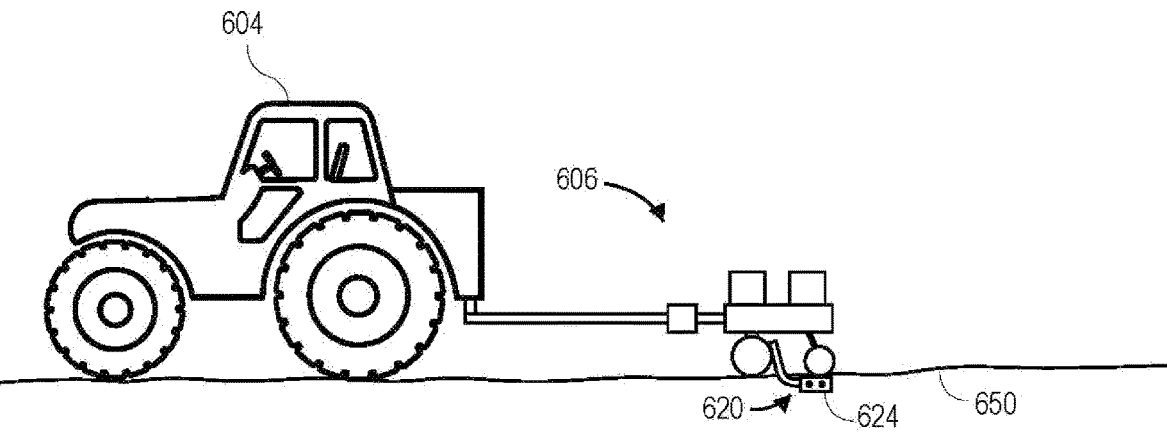
FIG. 6

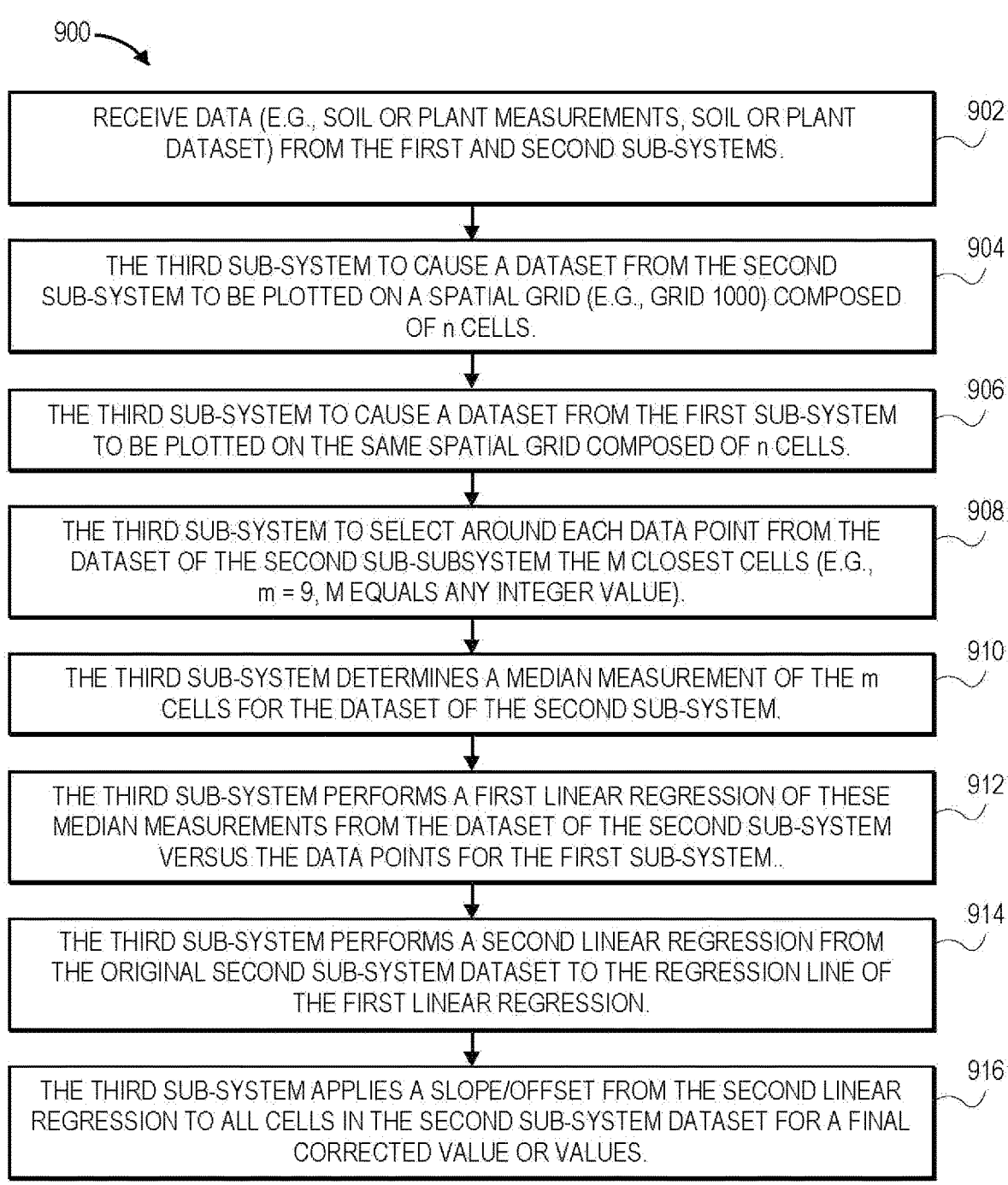

900

RECEIVE DATA (E.G., SOIL OR PLANT MEASUREMENTS, SOIL OR PLANT DATASET) FROM THE FIRST AND SECOND SUB-SYSTEMS.          902

THE THIRD SUB-SYSTEM TO CAUSE A DATASET FROM THE SECOND SUB-SYSTEM TO BE PLOTTED ON A SPATIAL GRID (E.G., GRID 1000) COMPOSED OF n CELLS.          904

THE THIRD SUB-SYSTEM TO CAUSE A DATASET FROM THE FIRST SUB-SYSTEM TO BE PLOTTED ON THE SAME SPATIAL GRID COMPOSED OF n CELLS.          906

THE THIRD SUB-SYSTEM TO SELECT AROUND EACH DATA POINT FROM THE DATASET OF THE SECOND SUB-SUBSYSTEM THE M CLOSEST CELLS (E.G., m = 9, M EQUALS ANY INTEGER VALUE).          908

THE THIRD SUB-SYSTEM DETERMINES A MEDIAN MEASUREMENT OF THE m CELLS FOR THE DATASET OF THE SECOND SUB-SYSTEM.          910

THE THIRD SUB-SYSTEM PERFORMS A FIRST LINEAR REGRESSION OF THESE MEDIAN MEASUREMENTS FROM THE DATASET OF THE SECOND SUB-SYSTEM VERSUS THE DATA POINTS FOR THE FIRST SUB-SYSTEM..          912

THE THIRD SUB-SYSTEM PERFORMS A SECOND LINEAR REGRESSION FROM THE ORIGINAL SECOND SUB-SYSTEM DATASET TO THE REGRESSION LINE OF THE FIRST LINEAR REGRESSION.          914

THE THIRD SUB-SYSTEM APPLIES A SLOPE/OFFSET FROM THE SECOND LINEAR REGRESSION TO ALL CELLS IN THE SECOND SUB-SYSTEM DATASET FOR A FINAL CORRECTED VALUE OR VALUES.          916

FIG. 9

HIGH AND LOW FREQUENCY SOIL AND PLANT ANALYSIS SYSTEMS WITH INTEGRATED MEASUREMENTS

CROSS-REFERENCE TO RELATED APPLICATIONS

This application is a national phase entry under 36 U.S.C. § 371 of International Patent Application PCT/IB2021/050819, filed Feb. 2, 2021 designating the United States of America and published in English as International Patent Publication WO 2021/214567 A1 on Oct. 28, 2021, which claims priority to U.S. Ser. No. 63/014,351, filed on 23 Apr. 2020, the contents of which are incorporated herein by reference in its entirety.

TECHNICAL FIELD

Embodiments of the present disclosure relate to high and low frequency agricultural soil and plant analysis systems with integrated measurements.

BACKGROUND

In recent years, the availability of advanced location-specific agricultural soil measurement systems (used in so-called "precision farming" practices) has increased grower interest in determining spatial variations in soil properties. However, soil sensors in soil and remote satellite soil sensing can both suffer from measurement accuracy issues.

BRIEF DESCRIPTION OF THE DRAWINGS

The present disclosure is illustrated by way of example, and not by way of limitation, in the figures of the accompanying drawings and in which:

FIG. 4 illustrates a soil and plant analysis apparatus in accordance with one embodiment.

FIGS. 5 and 6 illustrate a soil and plant analysis apparatus in accordance with another embodiment.

FIG. 9 illustrates a flow diagram of one embodiment for a method 900 of combining soil or plant measurements that are received from first and second sub-systems of a soil and plant analysis apparatus.

BRIEF SUMMARY

A soil or plant analysis apparatus to perform low and high frequency measurements is described herein. In one embodiment, the soil analysis apparatus comprises a first sub-system to perform low frequency soil measurements and a second sub-system to perform high frequency soil measurements. The high frequency measurements of the second sub-system have a frequency that is at least 1.25 times a frequency of the low frequency measurements of the first sub-system.

DETAILED DESCRIPTION

High and Low Frequency Soil and Plant Analysis Systems

Described herein are systems, machines, and implements having high and low frequency soil and plant analysis sensors for soil and plant analysis. The high and low frequency measurements allow a potentially quicker, higher resolution, and lower accuracy measurement to be corrected by a less frequent, higher accuracy measurement. The terms high frequency and low frequency are relative to each other, and they are defined by a ratio described below. High frequency is any frequency that is higher than low frequency, and low frequency is any frequency that is lower than high frequency.

In the following description, numerous details are set forth. It will be apparent, however, to one skilled in the art, that embodiments of the present disclosure may be practiced without these specific details. In some instances, well-known structures and devices are shown in block diagram form, rather than in detail, in order to avoid obscuring the present disclosure.

Figure 1:
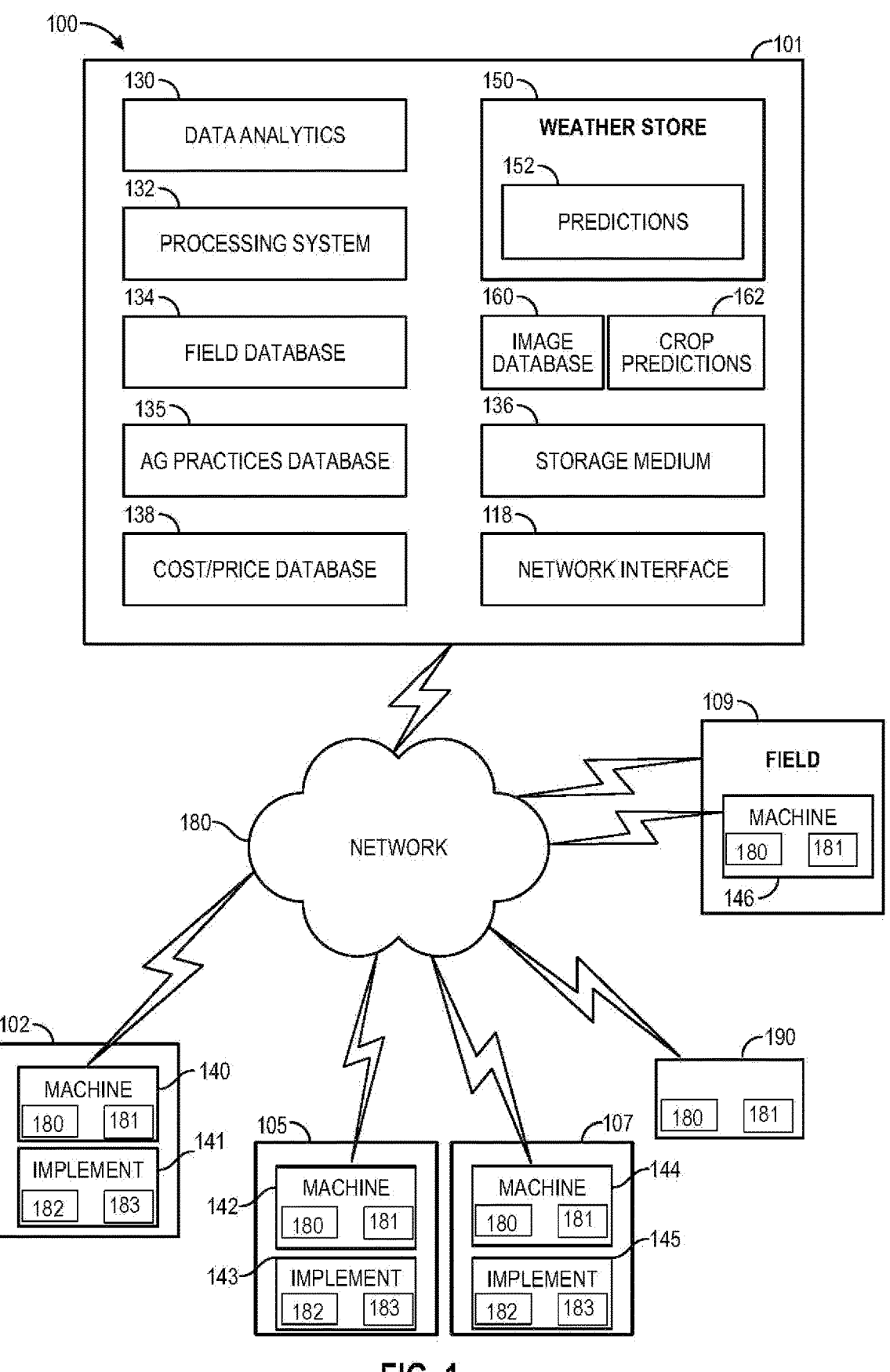
FIG. 1 shows an example of a system 100 for performing agricultural operations (e.g., high and low frequency soil and plant analysis, sensing soil and agricultural plant characteristics, applying fluid applications to plants) of agricultural fields in accordance with one embodiment.

FIG. 1 shows an example of a system 100 for performing agricultural operations (e.g., high and low frequency soil and plant analysis, sensing soil and agricultural plant characteristics, applying fluid applications to plants) of agricultural fields in accordance with one embodiment. For example and in one embodiment, the system 100 may be implemented as a cloud based system with servers, data processing devices, computers, etc. Aspects, features, and functionality of the system 100 can be implemented in a laboratory testing device, planters, planter monitors, All-terrain vehicle, Utility Terrain Vehicle, Pick-up truck, Combine Harvester, Tractor, Planter, Seeder, Drill, Fertilizer Spreader, Sprayer, Plow, Harrow, Disk, Ripper, irrigation implement (e.g., Center pivot irrigator), Tillage equipment, sidedress bars, servers, laptops, tablets, computer terminals, client devices, aviation device 190 (e.g., airplane 190, aerial drone device), handheld computers, personal digital assistants, cellular telephones, cameras, smart phones, mobile phones, computing devices, or a combination of any of these or other data processing devices. A laboratory device is a device is a stand alone device for analyzing samples. It can be stationed in a laboratory, or it can be used elsewhere not on a vehicle.

In other embodiments, the system 100 includes a network computer or an embedded processing device within another device (e.g., display device) or within a machine (e.g., planter, combine), or other types of data processing systems having fewer components or perhaps more components than that shown in FIG. 1. The system 100 (e.g., cloud based system) can sense soil and plants for soil and plant analysis using one or more of an implement (e.g., Planter, Seeder, Drill, Fertilizer Spreader, Sprayer, Plow, Harrow, Disk, Ripper, Center pivot irrigator, Tillage equipment), a machine (e.g., translatable self-propelled or pulled machine, vehicle, All-terrain vehicle, Utility Terrain Vehicle, Pick-up truck, Combine Harvester, Tractor), and an aviation device, or in a laboratory device. The system 100 includes machines 140, 142, 144, 146 and implements 141, 143, 145 coupled to a respective machine 140, 142, 144, 146. The implements can include sub-systems 182, 183 and the machines and aviation devices can include sub-systems 180, 181 with sensors for sensing soil and plants within associated fields (e.g., fields 102, 105, 107, 109).

The system 100 includes an agricultural analysis system 101 that includes a weather store 150 with current and historical weather data, weather predictions module 152 with weather predictions for different regions, and at least one processing system 132 for executing instructions for controlling and monitoring different operations (e.g., soil and plant measurements). The storage medium 136 may store instructions, software, software programs, etc. for execution by the processing system and for performing operations of the agricultural analysis system 102. In one example, storage medium 136 may contain a plant sensing prescription (e.g., plant sensing prescription that relates georeferenced positions in the field to locations of plants, plant data for each plant). The implement 141 (or any of the implements) may include sensors, a pump, flow sensors and/or flow controllers that may be specifically the elements that are in communication with the network 180 for sending control signals or receiving as-applied data.

An image database 160 stores captured images of crops at different growth stages. A data analytics module 130 may perform analytics on agricultural data (e.g., images, weather, field, yield, etc.) to generate crop predictions 162 relating to agricultural operations.

A field information database 134 stores agricultural data (e.g., sensed data for determining plant characteristics (e.g., stalk diameter, plant dimensions), crop growth stage, soil types, sensed data for determining soil characteristics, moisture holding capacity, etc.) for the fields that are being monitored by the system 100. An agricultural practices information database 135 stores farm practices information (e.g., as-applied planting information, as-applied spraying information, as-applied fertilization information, planting population, applied nutrients (e.g., nitrogen), yield levels, proprietary indices (e.g., ratio of seed population to a soil parameter), etc.) for the fields that are being monitored by the system 100. An implement can obtain fluid application data from the application units and provide this data to the system 100. A cost/price database 138 stores input cost information (e.g., cost of seed, cost of nutrients (e.g., nitrogen)) and commodity price information (e.g., revenue from crop).

The system 100 shown in FIG. 1 may include a network interface 118 for communicating with other systems or devices such as drone devices, user devices, and machines (e.g., planters, combines) via a network 180 (e.g., Internet, wide area network, WiMax, satellite, cellular, IP network, etc.). The network interface includes one or more types of transceivers for communicating via the network 180.

The processing system 132 may include one or more microprocessors, processors, a system on a chip (integrated circuit), or one or more microcontrollers. The processing system includes processing logic for executing software instructions of one or more programs. The system 100 includes the storage medium 136 for storing data and programs for execution by the processing system. The storage medium 136 can store, for example, software components such as a software application for sensing plant data or any other software application. The storage medium 136 can be any known form of a machine readable non-transitory storage medium, such as semiconductor memory (e.g., flash; SRAM; DRAM; etc.) or non-volatile memory, such as hard disks or solid-state drive.

While the storage medium (e.g., machine-accessible non-transitory medium) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Figure 2:
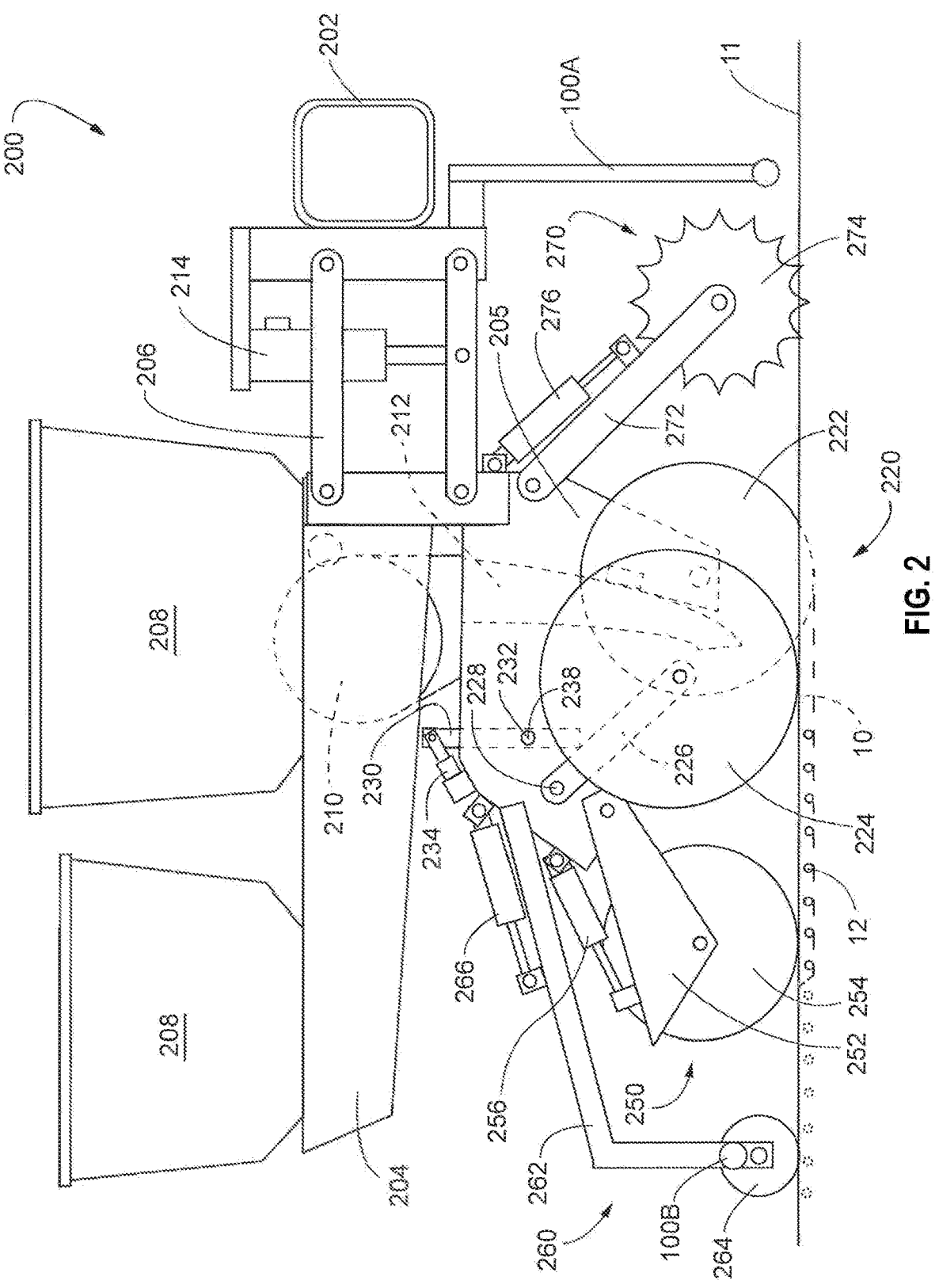
FIG. 2 is a side elevation view of an embodiment of a planter row unit.

Turning to FIG. 2, an embodiment is illustrated in which the row unit 200 is a planter row unit. FIG. 2 illustrates one example of a particular application of the soil and plant analysis sensors 100 as described herein that are disposed on a row unit 200 of an agricultural planter. The row unit 200 includes a soil and plant analysis sensor 100A disposed on a forward end of the row unit 200 and a soil and plant analysis sensor 100B disposed rearward end of the row unit 200. The soil and plant analysis sensors 100A, 100B may be above ground 11 for certain applications (e.g., plant contact sensing, remote soil or plant sensing) or below ground 11 for other applications (e.g., soil contact sensing).

With respect to FIG. 2, the row unit 200 is comprised of a frame 204 pivotally connected to the toolbar 202 by a parallel linkage 206 enabling each row unit 200 to move vertically independently of the toolbar 202. The frame 204 operably supports one or more hoppers 208, a seed meter 210, a seed delivery mechanism 212, a downforce control system 214, a seed trench opening assembly 220, a trench closing assembly 250, a packer wheel assembly 260, and a row cleaner assembly 270. It should be understood that the row unit 200 shown in FIG. 2 may be for a conventional planter or the row unit 200 may be a central fill planter, in which case the hoppers 208 may be replaced with one or more mini-hoppers and the frame 204 modified accordingly as would be recognized by those of skill in the art.

The downforce control system 214 is disposed to apply lift and/or downforce on the row unit 200 such as disclosed in U.S. Publication No. US2014/0090585.

The seed trench opening assembly 220 includes a pair of opening discs 222 rotatably supported by a downwardly extending shank member 205 of the frame 204. The opening discs 222 are arranged to diverge outwardly and rearwardly so as to open a v-shaped trench 10 in the soil 11 as the planter traverses the field. The seed delivery mechanism 212, such as a seed tube or seed conveyor, is positioned between the opening discs 222 to deliver seed 12 from the seed meter 210 and deposit it into the opened seed trench 10. The depth of the seed trench 10 is controlled by a pair of gauge wheels 224 positioned adjacent to the opening discs 222. The gauge wheels 224 are rotatably supported by gauge wheel arms 226 which are pivotally secured at one end to the frame 204 about pivot pin 228. A rocker arm 230 is pivotally supported on the frame 204 by a pivot pin 232. It should be appreciated that rotation of the rocker arm 230 about the pivot pin 232 sets the depth of the trench 10 by limiting the upward travel of the gauge wheel arms 226 (and thus the gauge wheels) relative to the opening discs 222. The rocker arm 230 may be adjustably positioned via a linear actuator 234 mounted to the row unit frame 204 and pivotally coupled to an upper end of the rocker arm 230. The linear actuator 234 may be controlled remotely or automatically actuated as disclosed, for example, in International Publication No. WO2014/186810.

A downforce sensor 238 is configured to generate a signal related to the amount of force imposed by the gauge wheels 224 on the soil. In some embodiments the pivot pin 232 for the rocker arm 230 may comprise the downforce sensor 238, such as the instrumented pins disclosed in U.S. Pat. No. 8,561,472. The seed meter 210 may be any commercially available seed meter, such as the fingertype meter or vacuum seed meter, such as the vSet® meter, available from Precision Planting LLC, 23207 Townline Rd, Tremont, IL 61568.

The trench closing assembly 250 includes a closing wheel arm 252 which pivotally attaches to the row unit frame 204. A pair of offset closing wheels 254 are rotatably attached to the closing wheel arm 252 and angularly disposed to direct soil back into the open seed trench so as to "close" the soil trench. An actuator 256 may be pivotally attached at one end to the closing wheel arm 252 and at its other end to the row unit frame 204 to vary the down pressure exerted by the closing wheels 254 depending on soil conditions. The closing wheel assembly 250 may be of the type disclosed in International Publication No. WO2014/066650.

The packer wheel assembly 260 comprises an arm 262 pivotally attached to the row unit fame 204 and extends rearward of the closing wheel assembly 250 and in alignment therewith.

The arm 262 rotatably supports a packer wheel 264. An actuator 266 is pivotally attached at one end to the arm and at its other end to the row unit frame 204 to vary the amount of downforce exerted by the packer wheel 264 to pack the soil over the seed trench 10.

The row cleaner assembly 270 may be the CleanSweep® system available from Precision Planting LLC, 23207 Townline Rd, Tremont, IL 61568. The row cleaner assembly 270 includes an arm 272 pivotally attached to the forward end of the row unit frame 204 and aligned with the trench opening assembly 220. A pair of row cleaner wheels 274 are rotatably attached to the forward end of the arm 272. An actuator 276 is pivotally attached at one end to the arm 272 and at its other end to the row unit frame 204 to adjust the downforce on the arm to vary the aggressiveness of the action of the row cleaning wheels 274 depending on the amount of crop residue and soil conditions.

It should be appreciated that rather than positioning the soil and plant analysis sensors 100 as shown in FIG. 2, the sensors may be positioned after the row cleaner assembly 270 and before the trench opening assembly 220 or in one or more other locations between the trench opening discs 222 and the closing wheels 254 or the packing wheel 264 depending on the soil region or characteristics of interest.

Figure 3:
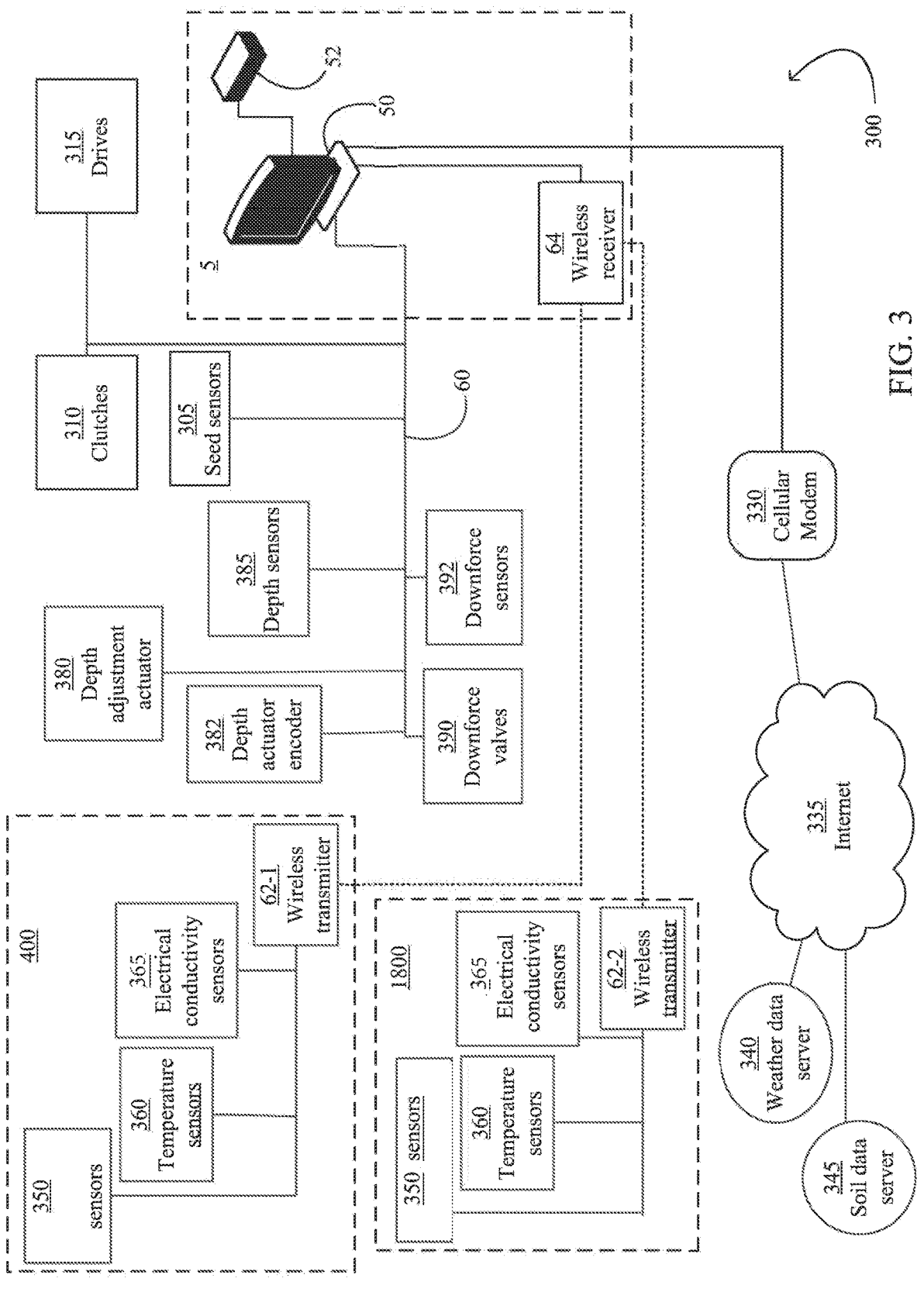
FIG. 3 schematically illustrates an embodiment of a soil and plant monitoring system.

Turning to FIG. 3, a soil and plant monitoring system 300 is schematically illustrated. The monitor 50 is preferably in data communication with components associated with each row unit 200 including the drives 315, the seed sensors 305, the GPS receiver 52, the downforce sensors 392, the valves 390, the depth sensors 385, the depth adjustment actuator 380, and the depth actuator encoders 382. In some embodiments, particularly those in which each seed meter 230 is not driven by an individual drive 315, the monitor 50 is also preferably in data communication with clutches 310 configured to selectively operably couple the seed meter 230 to the drive 315.

Continuing to refer to FIG. 3, the monitor 50 is preferably in data communication with a cellular modem 330 or other component configured to place the monitor 50 in data communication with the Internet, indicated by reference numeral 335. The internet connection may comprise a wireless connection or a cellular connection. Via the Internet connection, the monitor 50 preferably receives data from a weather data server 340 and a soil/plant data server 345. Via the Internet connection, the monitor 50 preferably transmits measurement data (e.g., soil and plant measurements described herein) to a recommendation server (which may be the same server as the weather data server 340 and/or the soil/plant data server 345) for storage and receives agronomic recommendations (e.g., planting recommendations such as planting depth, whether to plant, which fields to plant, which seed to plant, or which crop to plant) from a recommendation system stored on the server; in some embodiments, the recommendation system updates the planting recommendations based on the measurement data provided by the monitor 50.

Continuing to refer to FIG. 3, the monitor 50 is also preferably in data communication with one or more temperature sensors 360 mounted to the planter 10 and configured to generate a signal related to the temperature of soil being worked by the planter row units 200. The monitor 50 is preferably in data communication with one or more sensors 350 (e.g., reflectivity, optical wavelength reflectance/absorption, electromagnetic wavelength reflectance/absorption, electrical current flow, Xray flourescence, Laser-Induced Breakdown Spectroscopy, Near Infrared Spectroscopy, Mid Infrared Spectroscopy, Far Infrared Spectroscopy, Xray Diffraction, Gamma Ray emission, Multi-Spectral Sensing, Short wave infrared, Ion-Selective Electrode, Chemical Field Effect Transistor, Microfluidics, Flow Injection Analysis, Inductively Coupled Plasma, UV Visible or Near Infrared Flourescence, Photoacoustic Spectroscopy) mounted to the planter 10 and configured to generate a signal related to the soil or plant being worked by the planter row units 200.

Referring to FIG. 3, the monitor 50 is preferably in data communication with one or more electrical conductivity sensors 365 mounted to the planter 10 and configured to generate a signal related to the temperature of soil being worked by the planter row units 200.

In some embodiments, a first set of sensors 350, temperature sensors 360, and electrical conductivity sensors 365 are mounted to a seed firmer 400 and disposed to measure soil characteristics, temperature and electrical conductivity, respectively, of soil in the trench 10. In some embodiments, a second set of sensors 350, temperature sensors 360, and electrical conductivity sensors 365 are mounted to a reference sensor assembly 1800 and disposed to measure soil characteristics, temperature and electrical conductivity, respectively, of the soil, preferably at a depth different than the sensors on the seed firmer 400.

In some embodiments, a subset of the sensors are in data communication with the monitor 50 via a bus 60 (e.g., a CAN bus). In some embodiments, the sensors mounted to the seed firmer 400 and the reference sensor assembly 1800 are likewise in data communication with the monitor 50 via the bus 60. However, in the embodiment illustrated in FIG. 3, the sensors mounted to the seed firmer the sensors mounted to the seed firmer 400 and the reference sensor assembly 1800 are in data communication with the monitor 50 via a first wireless transmitter 62-1 and a second wireless transmitter 62-2, respectively. The wireless transmitters 62 at each row unit are preferably in data communication with a single wireless receiver 64 which is in turn in data communication with the monitor 50. The wireless receiver may be mounted to the toolbar 14 or in the cab of the tractor 5.

Each sub-system of a soil and plant analysis system can use sensing technology including but not limited to: optical wavelength reflectance/absorption values, electromagnetic wavelength reflectance/absorption values, temperature, electrical current flow, electrical conductivity, Xray flourescence, Laser-Induced Breakdown Spectroscopy, Near Infrared Spectroscopy, Mid Infrared Spectroscopy, Far Infrared Spectroscopy, Xray Diffraction, Gamma Ray emission, Multi-Spectral Sensing, Short wave infrared, Ion-Selective Electrode, Chemical Field Effect Transistor, Microfluidics, Flow Injection Analysis, Inductively Coupled Plasma, UV Visible or Near Infrared Flourescence, Photoacoustic Spectroscopy.

Each sub-system could have various potential embodiments in regards to proximity to the soil including but not limited to direct physical contact with the soil (or plant) and remote measurements of soil or plants with no direct physical contact to soil or plants.

The direct measurement apparatuses can be mounted on the one of the following vehicles or equipment including but not limited to: Planter, Seeder, Drill, Fertilizer Spreader, Sprayer, Plow, Harrow, Disk, Ripper, Center pivot irrigator, Tillage equipment, translatable self-propelled or pulled machine, vehicle, All-terrain vehicle, Utility Terrain Vehicle, Pick-up truck, Combine Harvester, Tractor.

For no direct physical contact applications, the remote measurement apparatuses could be mounted on any of the previously mentioned vehicles or equipment, but also on aerial devices such as airplane, drone, satellite (e.g., satellite imagery), etc. Also, samples can be collected and tested in a laboratory testing device.

Each sub-system could have various potential embodiments in regards to soil preparation including but not limited to the following embodiments. In a first example, the soil could receive no preparation, but simply be in native field conditions, and the measurement apparatus could directly measure the soil properties.

In a second example, a soil solution could be created by adding a diluent or extractant, followed by using the measurement apparatus to measure the properties in the soil solution. The extractant is specifically chosen for extracting a chemical to be tested. In some embodiments, the diluent or extractant is water. In other embodiments, the extractant is any chemical extractant used to test for nutrients in soil and/or vegetation. Examples of extractants include, but are not limited to water, Mehlich 3 extractant, NaCl, DTPA (diethylenetriaminepentaacetic acid), AB-DTPA (ammonium bicarbonate-diethylenetriaminepentaacetic acid), Mehlich 1, Mehlich 2, Mehlich 3, $NH_4OAc$, Olsen P test extractant, Morgan extractant, Modified Morgan extractant, Bray-Kurtz extractant, $CaCl_2$, $BaCl_2$, $SrCl_2$, Hot Water, Truog extractant, Ambic extractant, $HNO_3$, LiCl, calcium-acetate-lactate, oxalate, citrate-bicarbonate-dithionite, HCl, acid ammonium oxalate.

In a third example, a soil "pellet" could be created by mechanically compressing the soil followed by using the measurement apparatus to measure the properties in the soil "pellet".

In a fourth example, a soil sample could be prepared by removing the water from the soil by a drying process followed by using the measurement apparatus to measure the properties in the soil.

In a fifth example, a soil sample could be prepared by mechanically smoothing or roughening the surface properties of the soil to assist in follow-up measurement method.

The soil and plant analysis system can measure different parameters including soil and plant measurements such as soil physical properties, soil chemical properties, soil mechanical properties, soil biological properties, and plant properties.

The soil physical properties include density, strength, texture, structure, moisture content, consistence, permeability, pore space, and mineralogy.

Soil chemical properties (extractable and non-extractable forms) include pH, buffer pH, Phosphorus, Potassium, Calcium, Magnesium, Cation Exchange Capacity, Organic Matter, Sulfur, Nitrate, Zinc, Sodium, Iron, Manganese, Molybdenum, Boron, Copper, Chlorine, Chloride, Iron, base saturation, Nitrate, Nitrite, Total Nitrogen, Ammonium, Phosphate, Orthophosphate, Polyphosphate, Total Phosphate, Cation Exchange Capacity, Percent Base Saturation of Cations, Soluble Salts, Organic Matter, Excess Lime, Active Carbon, Aluminum, Amino Sugar Nitrate, Ammoniacal Nitrogen, Carbon:Nitrogen Ratio, Electrical Conductivity, Texture (Sand, Silt, Clay), Cyst nematode egg counts, and Mineralizable Nitrogen.

Soil mechanical properties includes shear strength, compressibility, erodability, elasticity, plasticity, available water capacity, plastic limit, liquid limit, specific gravity, etc.

Soil biological properties include mineralization potential, CO2 burst, Nematode analysis, and Cyst nematode.

Plants/vegetation measured properties include Nitrogen, Nitrate, Phosphorus, Potassium, Magnesium, Calcium, Sodium, Percent Base Saturation of Cations, Sulfur, Zinc, Manganese, Iron, Copper, Boron, Ammoniacal Nitrogen, Carbon, Chloride, Cobalt, Molybdenum, Selenium, Total Nitrogen, and live plant parasitic nematode.

In one example, a measurement frequency can be represented by the following units but is not limited to Measurements/area (e.g., acre, hectare, $m^2$, $ft^2$), Measurements/time, Measurements/distance (e.g., foot, meter, kilometer, etc), Measurements/grid with a grid being a pattern of polygonal shapes superimposed on a field, measurements/zone with a zone being an irregular shape superimposed onto a field.

FIG. 4 illustrates a soil and plant analysis apparatus in accordance with one embodiment. The soil analysis apparatus 400 can be self-propelled or pulled by a tractor 402 or machine. The soil and plant analysis apparatus 400 includes a sub-system 410 and a sub-system 420. In one example, a diluent can be added to sub-system 410 and soil and plant properties are measured with a flow injection analysis system. The sub-system 420 (e.g., soil collection knife, plant collection knife) may include soil/plant collection probe 422 and a sensor 424 (e.g., NIR sensor) in direct contact with soil or plant tissue. The sensor 424 can be mounted to the sub-system 420. The sensor 424 can be above, near, or below a soil surface level 450 depending a soil or plant analysis application. Alternatively, soil or plant samples can be collected and then tested on a laboratory device separate from the vehicle.

FIGS. 5 and 6 illustrate a soil and plant analysis apparatus in accordance with another embodiment. The soil and plant analysis apparatus 600 can be self-propelled or pulled by a tractor 502, 604, or machine. The soil and plant analysis apparatus 600 includes a sub-system 610 in FIG. 5 and a sub-system 620 in FIG. 6. The sub-system 610 may include a sensor 612 (e.g., laser-induced breakdown spectroscopy (LIBS) probe sensor) in direct contact with soil or plants to measure soil or plant properties with laser-induced break-down spectroscopy. The sensor 612 can be mounted to the sub-system 610.

In one example, the sub-system 620 may include a sensor 624 (e.g., VIS-NIR sensor) in direct contact with soil to sense soil properties. The sensor 624 can be mounted to the sub-system 620, which can be connected or mounted to an implement 606 (e.g., planter 606). The sensors 612 and 624 can be above, near, or below a soil surface level 650.

Figures 7, 8:
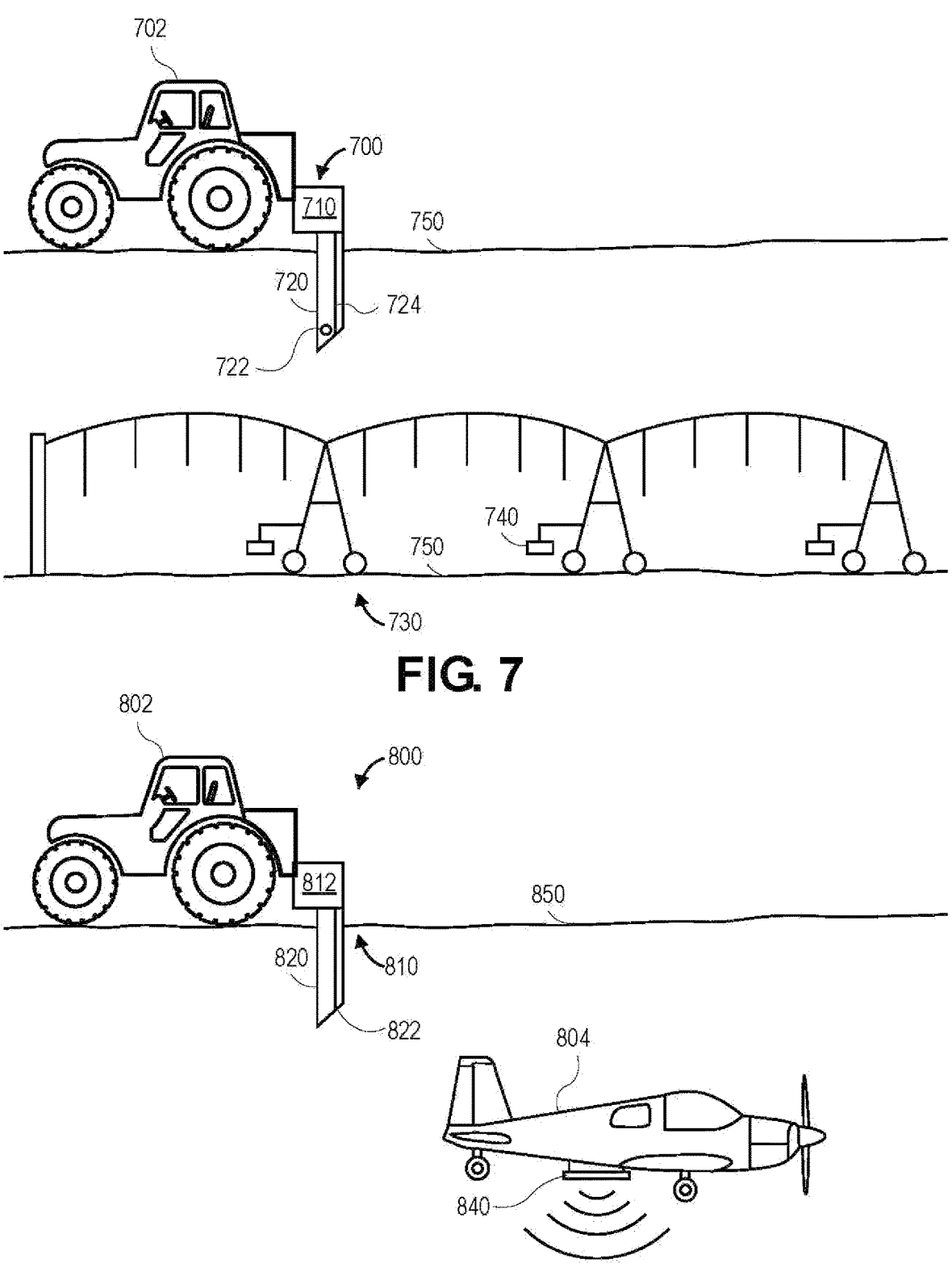
FIG. 7 illustrates a soil and plant analysis apparatus in accordance with another embodiment.
FIG. 8 illustrates a soil and plant analysis apparatus in accordance with another embodiment.

FIG. 7 illustrates a soil and plant analysis apparatus in accordance with another embodiment. The soil and plant analysis apparatus 700 can be self-propelled or pulled by a tractor 702 or machine. The soil and plant analysis apparatus 700 includes a sub-system 710 having a knife 720 with a sensor 722 and soil/plant collection probe 724. A sub-system 740 can be mounted to an irrigation system 730 (e.g., center pivot irrigator) or a different type of implement. In one example, the sub-system 710 can compress soil/plant tissue into a small sample (e.g., pellet), which is then analyzed by xray diffraction. The knife 720 includes the soil/plant probe 724 to obtain soil or plant tissue from a field and provide this soil or plant tissue as an input to the sub-system 710. The knife 720 includes an xray diffraction sensor 722 to sense soil or plant properties. The sub-system 740 performs non-contact soil/plant sensing using a Gamma ray emission technique. The sensor 722 can be positioned above, near, or below a soil surface level 750 while the sub-system 740 is positioned above the soil surface level for the Gamma ray emission technique.

FIG. 8 illustrates a soil and plant analysis apparatus in accordance with another embodiment. The soil and plant analysis apparatus 800 includes a sub-system 810 and a sub-system 840. The sub-system 810 can be self-propelled or pulled by a tractor 802 or machine. In one example, a diluent can be added to analysis unit 812 of sub-system 810 and soil/plant properties are measured with an ion selective electrode. The soil collection knife 820 of the sub-system 810 may include soil/plant tissue collection probe 822. The knife 820 can be positioned below the soil surface level 850.

The sub-system 840 includes a multi-spectral sensor with the sub-system 840 being mounted or integrated with an aviation device 804. The multi-spectral sensor measures soil or plant characteristics without contacting the soil or plant tissue.

In one example of a first embodiment, a soil analysis apparatus includes a first sub-system (e.g., 180, 182, 410, 420, 424, 610, 620, 624, 720, 722, 740, 810, 840, sensors 1252, probe 1255, sensors 1212) that performs low fre-quency soil measurements and a second sub-system (e.g., 181, 183, 410, 420, 424, 610, 620, 624, 720, 722, 740, 810, 840, sensors 1252, probe 1255, sensors 1212) that performs high frequency soil measurements. A first frequency of the high frequency measurement of the second sub-system and a second frequency of the low frequency measurement of the first sub-system have a frequency ratio of at least 1.25. In one example, the frequency ratio (e.g., 1.25, 1.5, 2, 3, 5, 10, etc.) is at least 1.25 and the low frequency measurements with higher accuracy can be used to improve accuracy for high frequency measurements with lower accuracy.

A third sub-system (e.g., processing system 132, process-ing system 1262, processing system 1220, processing sys-tem 132) is configured to combine measurements from the first sub-system with measurements from the second subsystem into a spatial map of soil properties that can be displayed on a display device (e.g., display device 1225, 1230, monitor 50).

In one example, the first and second sub-systems are one or more of the following: mechanically coupled, in fluid communication, or in electrical communication with each other.

The first sub-system and second sub-system are both attached to a single vehicle or attached pieces of equipment in a field. The measurement accuracy of the first sub-system can be at least 25% better than the measurement accuracy of the second sub-system.

In one example of a second embodiment, a soil analysis apparatus includes a first sub-system (e.g., 180, 182, 410, 420, 424, 610, 620, 624, 720, 722, 740, 810, 840, sensors 1252, probe 1255, sensors 1212) that performs high accu-racy soil measurements and a second sub-system (e.g., 181, 183, 410, 420, 424, 610, 620, 624, 720, 722, 740, 810, 840, sensors 1252, probe 1255, sensors 1212) that performs low accuracy soil measurements. The high measurement accu-racy of the first sub-system is at least 1.25 times (e.g., 1.25 times, 1.5 times, 2 times, 3 times, etc.) the low measurement accuracy of the second sub-system.

A third sub-system (e.g., processing system 132, process-ing system 1262, processing system 1220, processing sys-tem 132) is configured to combine measurements from the first sub-system with measurements from the second sub-system into a spatial map of soil properties that can be displayed on a display device (e.g., display device 1225, 1230, monitor 50).

In one example, the first and second sub-systems are one or more of the following: mechanically coupled, in fluid communication, or in electrical communication with each other.

The first sub-system and second sub-system are both attached to a single vehicle or attached pieces of equipment in a field. The high and low accuracy measurements allow a potentially quicker, higher resolution, and lower accuracy measurement to be corrected by a less frequent, higher accuracy measurement.

In one example of a third embodiment, a plant analysis apparatus includes a first sub-system (e.g., 180, 182, 410, 420, 424, 610, 620, 624, 720, 722, 740, 810, 840, sensors 1252, probe 1255, sensors 1212) that performs low fre-quency plant measurements and a second sub-system (e.g., 181, 183, 410, 420, 424, 610, 620, 624, 720, 722, 740, 810, 840, sensors 1252, probe 1255, sensors 1212) that performs high frequency plant measurements. The high frequency measurements of the second sub-system can be greater than 1.25 times the low frequency measurements of the first sub-system. In one example, the frequency ratio (e.g., 1.25, 1.5, 2, 3, 5, 10, etc.) between high and low frequency measurements is at least 1.25.

A third sub-system (e.g., processing system 132, process-ing system 1262, processing system 1220, processing sys-tem 132) is configured to combine measurements from the first sub-system with measurements from the second sub-system into a spatial map of plant properties that can be displayed on a display device (e.g., display device 1225, 1230, monitor 50).

In one example, the first and second sub-systems are one or more of the following: mechanically coupled, in fluid communication, or in electrical communication with each other.

The first sub-system and second sub-system are both attached to a single vehicle or attached pieces of equipment in a field. The measurement accuracy of the first sub-system can be at least 25% better than the measurement accuracy of the second sub-system.

In one example of a fourth embodiment, a plant analysis apparatus includes a first sub-system (e.g., 180, 182, 410, 420, 424, 610, 620, 624, 720, 722, 740, 810, 840, sensors 1252, probe 1255, sensors 1212) that performs high accuracy soil measurements and a second sub-system (e.g., 181, 183, 410, 420, 424, 610, 620, 624, 720, 722, 740, 810, 840, sensors 1252, probe 1255, sensors 1212) that performs low accuracy soil measurements. The high measurement accuracy of the first sub-system is at least 1.25 times (e.g., 1.25 times, 1.5 times, 2 times, 3 times, etc.) the low measurement accuracy of the second sub-system.

A third sub-system (e.g., processing system 132, processing system 1262, processing system 1220, monitor 50) is configured to combine measurements from the first sub-system with measurements from the second sub-system into a spatial map of plant properties that can be displayed on a display device (e.g., display device 1225, 1230, monitor 50). The measurements may include any measurements for analysis of plant tissue including nitrate temporal measurements.

In an example, the high frequency measurement occurs at 10 measurements per acre, and the low frequency measurement occurs at 4 measurements per acre, resulting in a ratio of 2.5:1, thus meeting the criteria (e.g., high frequency measurement of the second sub-system can be greater than 1.25 times the low frequency measurement of the first sub-system).

In another example, the high frequency measurement occurs at 1200 measurements per second, and the low frequency measurement occurs at 2 measurements per second, resulting in a ratio of 600:1.

Soil analysis measurement accuracy is calculated by comparing measured values with comparable soil lab values. For example, in the case of a soil phosphate measurement, the measurement accuracy is calculated by the following equation:

$$|Lab\ Phosphate–Soil\ analysis\ measured\ phosphate|/\ lab\ Phosphate.$$

In one example, (|20 ppm–25 ppm)/20 ppm) *100%=25%, given 20 ppm for Lab Phosphate, 25 ppm for soil analysis measured phosphate, and 20 ppm for Lab Phosphate.

A third sub-system is capable of combining measurements that are received from other sub-systems. There are many ways for the third sub-system 3 to combine the measurements from the first and second sub-system.

In one example, it is assumed that the high frequency data from the second sub-system is the "primary" data that will be operated on, since it has the benefit of a greater resolution than the data from the first system.

FIG. 9 illustrates a flow diagram of one embodiment for a method 900 of combining soil or plant measurements that are received from first and second sub-systems of a soil and plant analysis apparatus. The method 900 is performed by hardware (circuitry, dedicated logic, etc.), software (such as is run on a general purpose computer system or a dedicated machine or a device), or a combination of both. In one embodiment, the method 900 is performed by a third sub-system (e.g., processing system 132 of cloud based processing entity, processing system 1262, processing system 1220, monitor 50) of a soil and plant analysis apparatus (e.g., apparatus 400, 600, 700, 800). The third sub-system can execute instructions of a software application or program with processing logic.

In any embodiment herein, at operation 902, a third sub-system of the soil and plant analysis system receives data (e.g., soil and plant measurements, soil and plant dataset) from the first and second sub-systems. At operation 904, the third sub-system to cause a dataset from the second sub-system to be plotted on a spatial grid (e.g., grid 1000) composed of n cells. At operation 906, the third sub-system to cause a dataset from the first sub-system to be plotted on the same spatial grid composed of n cells.

At operation 908, the third sub-system to select around each data point from the dataset of the second sub-subsystem the m closest cells (e.g., m=9, m equals any integer value). At operation 910, the third sub-system determines a median measurement of the m cells for the dataset of the second sub-system.

At operation 912, the third sub-system performs a first linear regression of these median measurements from the dataset of the second sub-system versus the data points for the first sub-system. This first linear regression generates new data points for the dataset of the second sub-system.

At operation 914, the third sub-system performs a second linear regression from the original second sub-system dataset to the regression line of the first linear regression that is associated with new/modified data points (e.g., soil or plant measurement data) for the second sub-system.

At operation 916, the third sub-system applies a slope/offset from the second linear regression to all cells in the second sub-system dataset for a final corrected value or values.

Figure 10A:
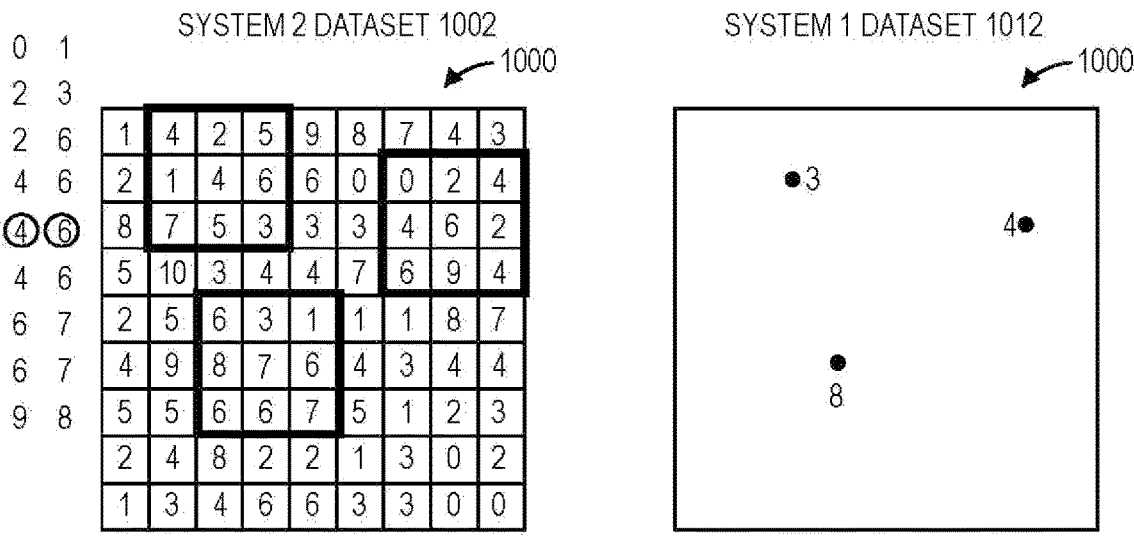
FIG. 10A illustrates plots of the datasets from the first and second sub-systems in accordance with one embodiment.

FIG. 10A illustrates plots of the datasets from the first and second sub-systems in accordance with one embodiment. The high frequency dataset 1002 from the second sub-system is plotted on a grid 1000. A low frequency dataset 1012 from the second sub-system is plotted on the same grid 1000.

Figure 10B:
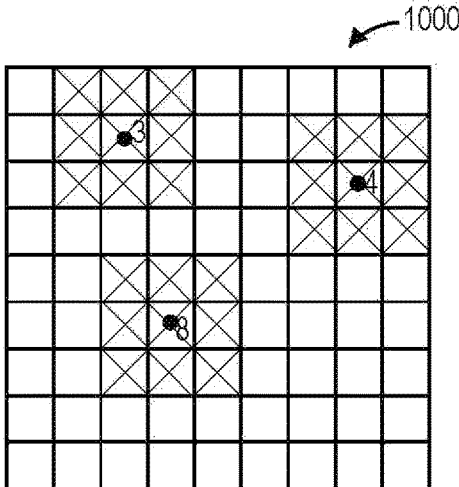
FIG. 10B illustrates an overlay of the datasets from the first and second sub-systems on the same grid 1000.

FIG. 10B illustrates an overlay of the datasets from the first and second sub-systems on the same grid 1000. The third sub-system to select around each data point from the dataset of the second sub-subsystem the m closest cells (e.g., m=9, m equals any integer value). The third sub-system determines a median measurement (e.g., 4,4,6) of the m cells for the dataset of the second sub-system. The third sub-system performs a first linear regression (e.g., y=0.4286x+2.5238, y=$2^{nd}$ sub-system, x=$1^{st}$ sub-system) of these median measurements from the dataset of the second sub-system versus the data points (e.g., 3, 4, 8) for the first sub-system.

The third sub-system perform a second linear regression (e.g., y=0.9644x+0.1665, y=$2^{nd}$ sub-system new values (3.8096, 4.2382, 5.9526), x=2nd sub-system original values (4,4,6)) from the original second sub-system dataset to the regression line from the first linear regression. The third sub-system applies this slope/offset from the second linear regression to all cells in the second sub-system dataset for a final corrected value (new values).

Figure 11:
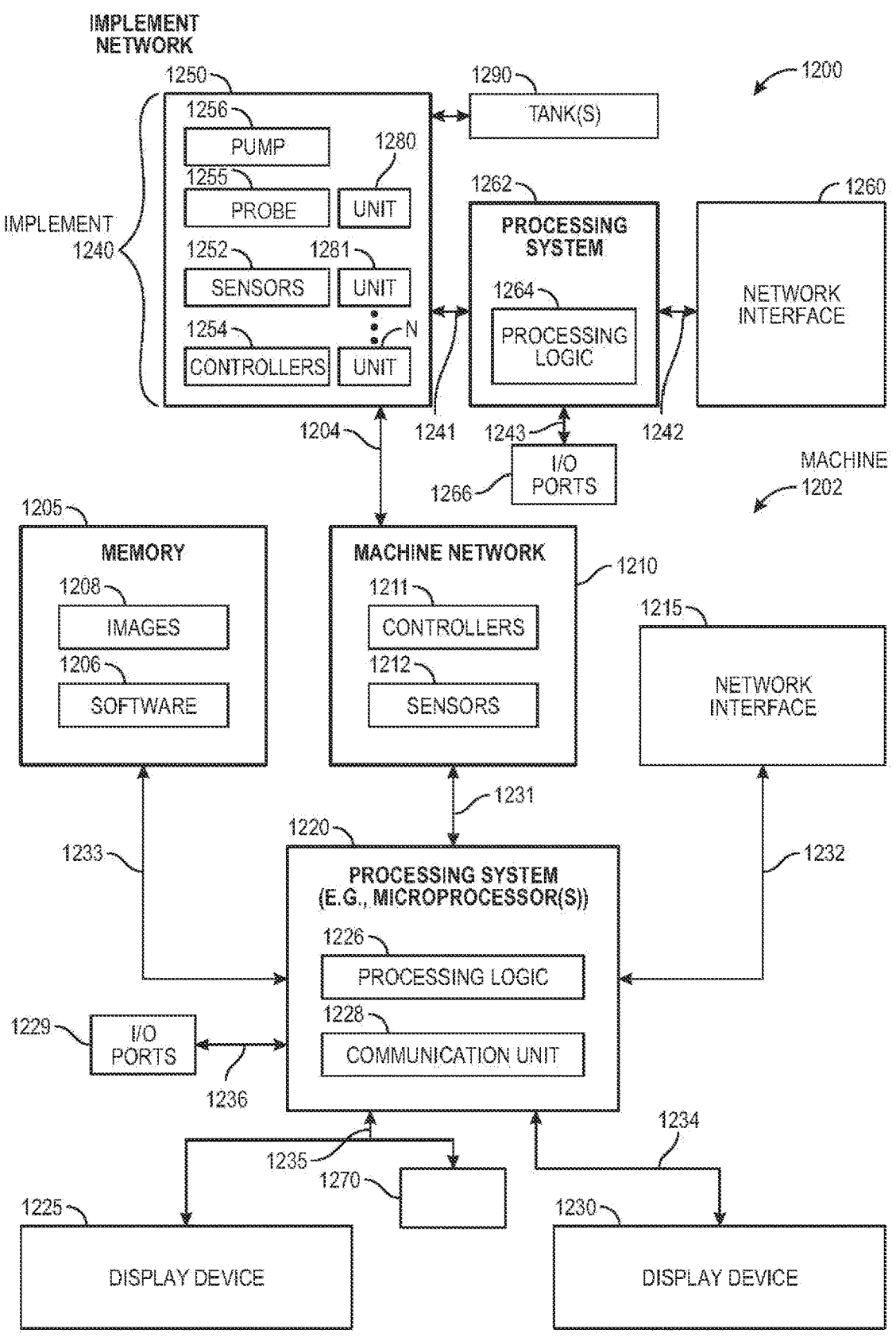
FIG. 11 shows an example of a soil and plant analysis system 1200 (apparatus 1200) that includes an implement 1240 (e.g., Planter, Seeder, Drill, Fertilizer Spreader, Sprayer, Plow, Harrow, Disk, Ripper, Center pivot irrigator, Tillage equipment) and a machine 1202 (e.g., translatable self-propelled or pulled machine, vehicle, All-terrain vehicle, Utility Terrain Vehicle, Pick-up truck, Combine Harvester, Tractor), in accordance with one embodiment.

FIG. 11 shows an example of a soil and plant analysis system 1200 (apparatus 1200) that includes an implement 1240 (e.g., Planter, Seeder, Drill, Fertilizer Spreader, Sprayer, Plow, Harrow, Disk, Ripper, Center pivot irrigator, Tillage equipment) and a machine 1202 (e.g., translatable self-propelled or pulled machine, vehicle, All-terrain vehicle, Utility Terrain Vehicle, Pick-up truck, Combine Harvester, Tractor), in accordance with one embodiment. The machine 1202 includes a processing system 1220, memory 1205, machine network 1210 (e.g., a controller area network (CAN) serial bus protocol network, an ISOBUS network, etc.), and a network interface 1215 for communicating with other systems or devices including the implement 1240. The machine network 1210 includes sensors 1212 (e.g., speed sensors, optical wavelength reflectance/absorption, electromagnetic wavelength reflectance/absorption, temperature, electrical current flow, electrical conductivity, Xray flourescence, Laser-Induced Breakdown Spectroscopy, Near Infrared Spectroscopy, Mid Infrared Spectroscopy, Far Infrared Spectroscopy, Xray Diffraction, Gamma Ray emission, Multi-Spectral Sensing, Short wave infrared, Ion-Selective Electrode, Chemical Field Effect Transistor, Microfluidics, Flow Injection Analysis, Inductively Coupled Plasma, UV Visible or Near Infrared Flourescence, Photoacoustic Spectroscopy), controllers 1211 (e.g., GPS receiver, radar unit) for controlling and monitoring operations of the machine or implement. The network interface 1215 can include at least one of a GPS transceiver, a WLAN transceiver (e.g., WiFi), an infrared transceiver, a Bluetooth transceiver, Ethernet, or other interfaces from communications with other devices and systems including the implement 1240. The network interface 1215 may be integrated with the machine network 1210 or separate from the machine network 1210 as illustrated in FIG. 12. The I/O ports 1229 (e.g., diagnostic/on board diagnostic (OBD) port) enable communication with another data processing system or device (e.g., display devices, sensors, etc.).

In one example, the machine performs operations of a tractor that is coupled to an implement for soil and plant analysis of a field. The soil and plant analysis data for each row unit of the implement can be associated with locational data at time of application to have a better understanding of the soil and plant analysis for each row and region of a field. Data associated with the soil and plant analysis can be displayed on at least one of the display devices 1225 and 1230. The display devices can be integrated with other components (e.g., processing system 1220, memory 1205, etc.) to form the monitor 50.

The processing system 1220 may include one or more microprocessors, processors, a system on a chip (integrated circuit), or one or more microcontrollers. The processing system includes processing logic 1226 for executing software instructions of one or more programs and a communication unit 1228 (e.g., transmitter, transceiver) for transmitting and receiving communications from the machine via machine network 1210 or network interface 1215 or implement via implement network 1250 or network interface 1260. The communication unit 1228 may be integrated with the processing system or separate from the processing system. In one embodiment, the communication unit 1228 is in data communication with the machine network 1210 and implement network 1250 via a diagnostic/OBD port of the I/O ports 1229.

Processing logic 1226 including one or more processors or processing units may process the communications received from the communication unit 1228 including agricultural data (e.g., GPS data, planting application data, soil characteristics, plant characteristics, any data sensed from sensors of the implement 1240 and machine 1202, etc.). The processing logic 1226 can process high and low frequency soil/plant measurements as described herein to determine soil and plant properties and characteristics. The system 1200 includes memory 1205 for storing data and programs for execution (software 1206) by the processing system. The memory 1205 can store, for example, software components such as soil and plant analysis software for analysis of soil and planting applications for performing operations of the present disclosure, or any other software application or module, images 1208 (e.g., captured images of crops, soil, furrow, soil clods, row units, etc.), alerts, maps, etc. The memory 1205 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

The processing system 1220 communicates bi-directionally with memory 1205, machine network 1210, network interface 1215, header 1280, display device 1230, display device 1225, and I/O ports 1229 via communication links 1231-1236, respectively. The processing system 1220 can be integrated with the memory 1205 or separate from the memory 1205.

Display devices 1225 and 1230 can provide visual user interfaces for a user or operator. The display devices may include display controllers. In one embodiment, the display device 1225 is a portable tablet device or computing device with a touchscreen that displays data (e.g., soil and plant analysis data, planting application data, captured images, localized view map layer, soil color data and images, high definition field maps of seed germination data, seed environment data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 1230 may be a display (e.g., display provided by an original equipment manufacturer (OEM)) that displays images and data for a localized view map layer, as-applied fluid application data, as-planted or as-harvested data, yield data, seed germination data, seed environment data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 1270 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 1240 includes an implement network 1250, a processing system 1262, a network interface 1260, and optional input/output ports 1266 for communicating with other systems or devices including the machine 1202. The implement network 1250 (e.g, a controller area network (CAN) serial bus protocol network, an ISOBUS network, etc.) includes a pump 1256 for pumping fluid from a storage tank(s) 1290 to application units 1280, 1281, . . . N of the implement, sensors 1252 (e.g., speed sensors, optical wavelength reflectance/absorption, electromagnetic wavelength reflectance/absorption, temperature, electrical current flow, electrical conductivity, Xray flourescence, Laser-Induced Breakdown Spectroscopy, Near Infrared Spectroscopy, Mid Infrared Spectroscopy, Far Infrared Spectroscopy, Xray Diffraction, Gamma Ray emission, Multi-Spectral Sensing, Short wave infrared, Ion-Selective Electrode, Chemical Field Effect Transistor, Microfluidics, Flow Injection Analysis, Inductively Coupled Plasma, UV Visible or Near Infrared Flourescence, Photoacoustic Spectroscopy seed sensors for detecting passage of seed, sensors for detecting characteristics of soil or a trench including soil moisture, soil organic matter, soil temperature, soil color, seed presence, seed spacing, percentage of seeds firmed, and soil residue presence, downforce sensors, actuator valves, moisture sensors or flow sensors for a combine, speed sensors for the machine, seed force sensors for a planter, fluid application sensors for a sprayer, or vacuum, lift, lower sensors for an implement, flow sensors, etc.) for sensing soil and plant properties and characteristics, probes 1255 for collecting soil and plant samples for the soil and plant analysis, controllers 1254 (e.g., GPS receiver), and the processing system 1262 for controlling and monitoring operations of the implement. The pump controls and monitors the application of the fluid to crops or soil as applied by the implement. The fluid application can be applied at any stage of crop development including within a planting trench upon planting of seeds, adjacent to a planting trench in a separate trench, or in a region that is nearby to the planting region (e.g., between rows of corn or soybeans) having seeds or crop growth. In other embodiments, the applicator can be granular material applicator or a combination of fluid applicator and granular material applicator.

For example, the controllers may include processors in communication with a plurality of seed sensors. The processors are configured to process data (e.g., fluid application data, seed sensor data, soil data, plant data, furrow or trench data) and transmit processed data to the processing system 1262 or 1220. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 1260 can be a GPS transceiver, a WLAN transceiver (e.g., WiFi), an infrared transceiver, a Bluetooth transceiver, Ethernet, or other interfaces from communications with other devices and systems including the machine 1202. The network interface 1260 may be integrated with the implement network 1250 or separate from the implement network 1250 as illustrated in FIG. 12.

The processing system 1262 communicates bi-directionally with the implement network 1250, network interface 1260, and I/O ports 1266 via communication links 1241-1243, respectively.

The implement communicates with the machine via wired and possibly also wireless bi-directional communications 1204. The implement network 1250 may communicate directly with the machine network 1210 or via the networks interfaces 1215 and 1260. The implement may also be physically coupled to the machine for agricultural operations (e.g., planting, harvesting, spraying, etc.). The memory 1205 may be a machine-accessible non-transitory medium on which is stored one or more sets of instructions (e.g., software 1206) embodying any one or more of the methodologies or functions described herein. The software 1206 may also reside, completely or at least partially, within the memory 1205 and/or within the processing system 1220 during execution thereof by the system 1200, the memory and the processing system also constituting machine-accessible storage media. The software 1206 may further be transmitted or received over a network via the network interface 1215.

What is claimed is:

1. A soil or plant analysis apparatus comprising:
a first sub-system to perform soil or plant measurements at a first measurement accuracy at a first measurement frequency represented by a first number of measurements per unit area; and
a second sub-system to perform soil or plant measurements at a second measurement accuracy at a second measurement frequency represented by a second number of measurements per unit area, wherein the second measurement frequency of the second sub-system is at least 1.25 times the first measurement frequency of the first sub-system, wherein the first measurement accuracy of the first sub-system is utilized to correct a lower measurement accuracy of the second measurement accuracy of the second sub-system.

2. The soil or plant analysis apparatus of claim 1, further comprising:
a third sub-system that is configured to combine measurements from the first sub-system with measurements from the second sub-system into a spatial map of soil or plant properties to be displayed on a display device.

3. The soil or plant analysis apparatus of claim 1, wherein the first and second sub-systems are one or more of mechanically coupled, in fluid communication, or in electrical communication with each other.

4. The soil or plant analysis apparatus of claim 1, wherein the first and second sub-systems are attached to a single All-terrain vehicle, Utility Terrain Vehicle, Pick-up truck, Combine Harvester, Tractor, Planter, Seeder, Drill, Fertilizer Spreader, Sprayer, Plow, Harrow, Disk, Ripper, irrigation implement, Tillage equipment, sidedress bars, or attached pieces of equipment in a field.

5. The soil or plant analysis apparatus of claim 1, wherein the first and second sub-systems are in a laboratory device.

6. The soil or plant analysis apparatus of claim 1, wherein a measurement accuracy of the first sub-system is at least 25 percent better than a measurement accuracy of the second sub-system, the measurement accuracy being calculated by comparing measured values with comparable soil lab values.

7. The soil or plant analysis apparatus of claim 6, wherein the plant measurements include nitrate temporal measurements of plant tissue.

8. The soil or plant analysis apparatus of claim 6, wherein the plant measurements at the second measurement frequency occur at 25 measurements per hectare or 10 measurements per acre, and the plant measurements at the first measurement frequency occur at 10 measurements per hectare or 4 measurements per acre.

9. The soil or plant analysis apparatus of claim 1, wherein one or more of the first and second sub-systems includes a first sensor to perform the soil or plant measurements at the first measurement frequency and a second sensor to perform the soil or plant measurements at the second measurement frequency.

10. The soil or plant analysis apparatus of claim 1, wherein the first or second sub-system performs non-contact soil sensing using a Gamma ray emission technique or the first or second sub-system includes a multi-spectral sensor that is mounted or integrated with an aviation device.

11. A soil and plant analysis system, comprising:
a soil or plant analysis apparatus according to claim 1;

a communication unit to receive soil or plant measurement data from the first and second sub-systems of the soil or plant analysis apparatus; and a processor coupled to the communication unit, the processor is configured to cause the soil or plant measurement data from the second sub-system to be plotted on a spatial grid having a plurality of cells and to cause the soil or plant measurement data from the first sub-system to be plotted on the same spatial grid.

12. The soil and plant analysis system of claim 11, wherein the processor is further configured to select m cells around each data point from the soil or plant measurement data of the second sub-system and to determine a median measurement of the m cells for the soil or plant measurement data of the second sub-system, m being a positive integer.

13. The soil and plant analysis system of claim 12, wherein the processor is further configured to perform a first linear regression of the median measurements from the second sub-system versus the soil or plant measurement data for the first sub-system.

14. The soil and plant analysis system of claim 13, wherein the processor is further configured to perform a second linear regression from the soil or plant measurement data of the second sub-system to a regression line of the first linear regression that is associated with modified soil or plant measurement data for the second sub-system.

15. The soil and plant analysis system of claim 14, wherein the processor is further configured to apply a slope or offset from the second linear regression to all cells in the soil or plant measurement data of the second sub-system for a final corrected value.

\* \* \* \* \*